(12) United States Patent
Giordano et al.

(10) Patent No.: US 7,643,868 B2
(45) Date of Patent: Jan. 5, 2010

(54) METHOD AND APPARATUS FOR DETERMINING THE POSITION OF THE TIBIAL EXIT POINT OF THE ANTERIOR CRUCIATE LIGAMENT

(75) Inventors: Nicola Giordano, Villingen-Schwenningen (DE); François Leitner, Uriage (FR); François Boux De Casson, Grenoble (FR); Juergen Eichhorn, Mittersfels/Scheibelsgrub (DE)

(73) Assignee: Aesculap AG, Tuttlingen (DE)

( * ) Notice: Subject to any disclaimer, the term of this patent is extended or adjusted under 35 U.S.C. 154(b) by 900 days.

(21) Appl. No.: 11/086,995

(22) Filed: Mar. 21, 2005

(65) Prior Publication Data

US 2005/0222574 A1    Oct. 6, 2005

Related U.S. Application Data

(63) Continuation of application No. PCT/EP02/10861, filed on Sep. 27, 2002.

(51) Int. Cl.
*A61B 5/05* (2006.01)
(52) U.S. Cl. .......... 600/429; 600/407; 600/595; 606/97
(58) Field of Classification Search .......... 606/96, 606/97, 53, 86; 607/60; 600/549, 429
See application file for complete search history.

(56) References Cited

U.S. PATENT DOCUMENTS

| 5,564,437 | A | 10/1996 | Bainville et al. |
| 5,743,909 | A | 4/1998 | Collette |
| 6,503,249 | B1 * | 1/2003 | Krause .................. 606/62 |
| 2002/0055679 | A1 * | 5/2002 | Sati et al. ............... 600/424 |
| 2002/0151894 | A1 * | 10/2002 | Melkent et al. .......... 606/61 |

FOREIGN PATENT DOCUMENTS

| EP | 0 603 089 | 6/1994 |
| WO | 99/23956 | 5/1999 |
| WO | WO 99/23956 | * 5/1999 |

* cited by examiner

*Primary Examiner*—Thomas C Barrett
*Assistant Examiner*—Andrew Yang
(74) *Attorney, Agent, or Firm*—Lipsitz & McAllister, LLC

(57) ABSTRACT

In order to establish an optimum position on the upper side of the tibia for the exit point of an anterior cruciate ligament replacement, it is proposed that, with the leg bent, the position of a number of points along the front edge of the notch is detected and in this way their position and progression on the femur are also determined, that, with the leg straight, the course of this front edge of the notch is projected onto a projection plane which is perpendicular to the longitudinal axis of the tibia in the region of the upper side of the tibia, and that, within the region enclosed by this projected curve, the exit point is selected such that it maintains at least a distance corresponding to the radius of the implant from the projected curve. Furthermore, an apparatus for carrying out such a method is proposed.

11 Claims, 3 Drawing Sheets

METHOD AND APPARATUS FOR DETERMINING THE POSITION OF THE TIBIAL EXIT POINT OF THE ANTERIOR CRUCIATE LIGAMENT

This application is a continuation of international application number PCT/EP02/10861 filed on Sep. 27, 2002.

The present disclosure relates to the subject matter disclosed in international application PCT/EP02/10861 of Sep. 27, 2002, which is incorporated herein by reference in its entirety and for all purposes.

BACKGROUND OF THE INVENTION

The invention relates to a method for determining the position on the upper side of the tibia of the exit point of an implant replacing the anterior cruciate ligament of a knee joint. The invention also relates to an apparatus for determining the position on the upper side of the tibia of the exit point of an implant replacing the anterior cruciate ligament of a knee joint, having a navigation system, having marking elements fixedly connected to the femur and the tibia, having a navigated sensor and having a data-processing system to which the positional data recorded by the navigation system can be fed.

When replacing an anterior cruciate ligament of a knee joint with an implant, it is extremely important for the implant to be positioned exactly. The implant is usually connected in a suitable way at its two ends to the femur and the tibia, respectively, for example by insertion in holes which are drilled in the femur and the tibia and the end points of which mark exit points for the implant on the surface of the femur and the surface of the tibia.

An important aspect here is that, when there is movement of the knee, the length of the implant is to remain as invariant as possible in the region between the exit points, in other words an isometry of the implant is to be achieved. For this purpose, it is known to determine the exit point of the implant on the femur by a method and an apparatus with which geometrical data of the femur surface are scanned and stored and with which these geometrical data are used to calculate the change in the isometry for different positions of the exit points (EP 603 089 B1). With this method, however, it is only possible to optimize the position of the exit point on the femur side; this known method cannot help with the selection of the exit point of the implant on the tibia side.

A major problem when determining the position of the exit point on the tibia side is that, when it is in the fitted state, the implant must remain free between the two exit points in all positions of the knee; it must therefore not be in contact with bone structures, for example specific surfaces of the femur, since this contact could lead to the implant being damaged. The anterior cruciate ligament and the implant replacing it are normally located in the interspace between the surfaces of the femur joint, that is the condyles, this interspace being referred to as the notch. This notch is bounded laterally by the side surfaces of the condyles, on the upper side by an upper roof area, and this roof area goes over into the lateral outer surface of the femur via a prominent front edge on the front side of the femur. If the implant of the anterior cruciate ligament is improperly positioned, it is precisely this front edge that can collide with this implant in certain positions of the leg, and this must be avoided in all cases.

Up until now, the surgeon has chosen the positioning of the tibial exit point of the anterior cruciate ligament on the basis of his experience, but misplaced implantations cannot in this case be ruled out with certainty.

It is an object of the invention to provide a method by which the surgeon is assisted in locating the tibial exit point in such a way that a free path for the implant is ensured in all positions of the leg.

SUMMARY OF THE INVENTION

This object is achieved according to the invention by a method of the type described at the beginning in which the positional data of the tibia and the femur are determined by means of a navigation system, in which geometrical form data of the femur in its region facing the upper side of the tibia are recorded and in which these data are processed together with the positional data of the tibia and the femur in a data-processing system to calculate the positional data for the exit point, with the following individual steps being performed:

with the leg bent, the position of a number of points along the front edge of the notch is detected and in this way their position and progression on the femur are determined, with the leg straight, the course of this front edge of the notch is projected onto a projection plane which is perpendicular to the longitudinal axis of the tibia in the region of the upper side of the tibia, and within the region enclosed by this projected curve, the exit point is selected such that it maintains at least a distance corresponding to the radius of the implant from the projected curve.

Whenever the exit point lies within the region of the projected curve which assumes a substantially U-shaped course, it is ensured that the implant will not collide with osseous structures of the femur for any movements of the knee, in particular with the front edge of the notch. The projection plane may in this case be selected at different distances from the femur; its precise position is unimportant as long as this plane is located only in the upper tibial region. All that is important for the surgeon is to find a suitable position for the exit point in this plane, and this information can also be achieved if the plane is displaced upward or downward by a few millimeters.

It may further be provided that a circular area of a diameter corresponding to the diameter of the implant used is projected into the projection plane, this area is displaced in the area enclosed by the projected curve such that it does not intersect the projected curve, and that in one of the positions of the circular area achieved in this way its center point is selected as the exit point for the implant. With this precondition it is ensured that the implant is always located in the region of the tibial exit point completely inside the projection area that is enclosed by the projected curve, and then a collision with the bone tissue of the femur is also ruled out.

It is particularly advantageous if a position of the exit point in which the latter lies as far as possible in the front part of the region enclosed by the projected curve and as close as possible to the projected curve is selected. As a result, the tibial exit point is shifted as far as possible to the front side of the knee joint, that is in the anterior direction. This increases the stability of the knee joint. Nevertheless, contact with the bone tissue of the femur is avoided.

According to a preferred embodiment, a navigated sensor is used for recording the positional data for the points located on the front edge of the notch, the position of which sensor is therefore likewise detected by means of the navigation system, so that the entire course of the front edge of the notch can be scanned point by point just by placing the sensor on the front edge of the notch and storing the corresponding positional data.

It may further be provided that, during the detection of the position of points on the front edge of the notch, an image of the front edge is shown on an image display of the data-processing system and the points for which the positional data are to be recorded are marked there. These points may comprise a proposal for the positions at which positional data are to be recorded by contact of a sensor, but it is also possible as an alternative or in addition to this to mark on this image display the points at which positional data have already been recorded, so that the surgeon can see in which regions sufficient positional data have already been recorded, and on the other hand in which regions further positional data still have to be recorded.

The method is made particularly easy for the surgeon if the projected curve and the region enclosed by it are presented on an image display, the desired position of the exit point is selected on this image display by means of a displaceable image of a display element and the corresponding positional data are stored in the data-processing system. The surgeon then only has to move this display element into the desired position in the region enclosed by the projected curve and he can select which position of the tibial exit point he prefers by storing the desired position. In any event, it is ensured that the implantation is performed without any collision with bone tissue of the femur.

A circle of a diameter corresponding to that of the implant used may be selected in particular as the display element; for example the diameter of the implant may be entered in the data-processing system and stored there prior to the operation.

The object is achieved by an apparatus of the type described at the beginning which is characterized by a memory in which positional data for a number of points along the front edge of the notch recorded with the leg bent can be stored, and by a computer unit which, with the leg straight, projects the positional data stored in the memory, and with it the course of the front edge of the notch, onto a projection plane in the region of the upper side of the tibia, which plane is perpendicular to the longitudinal axis of the tibia. This is a process which is carried out automatically by the data-processing system and by which a region on the surface of the tibia which is enclosed by the projected curve and in which the desired exit point lies is defined.

In this case it is advantageous if the computer unit projects a circular area of a diameter corresponding to the diameter of the implant used into the projection plane and displaces it in the area enclosed by the projected curve such that it does not intersect the projected curve, and if in one of the positions of the circular area achieved in this way its center point is selected as the exit point for the implant.

In particular, it may be provided that the computer unit selects a position for the exit point in which the latter lies as far as possible in the front part of the region enclosed by the projected curve and as close as possible to the projected curve.

In the case of a preferred embodiment, during the detection of the position of points on the front edge of the notch, the data-processing system forms an image of the front edge on an image display and marks there the points for which the positional data are to be recorded.

It is advantageous if the computer unit presents the projected curve and the region enclosed by it on an image display, also shows a displaceable image of a display element for the selected position of the exit point on this image display and stores the corresponding positional data for the selected position in a memory. In particular, the display element may have the form of a circle of a diameter corresponding to that of the implant used.

The following description of preferred embodiments of the invention serves for a more detailed explanation in conjunction with the drawing.

DETAILED DESCRIPTION OF THE INVENTION

Figure 1:
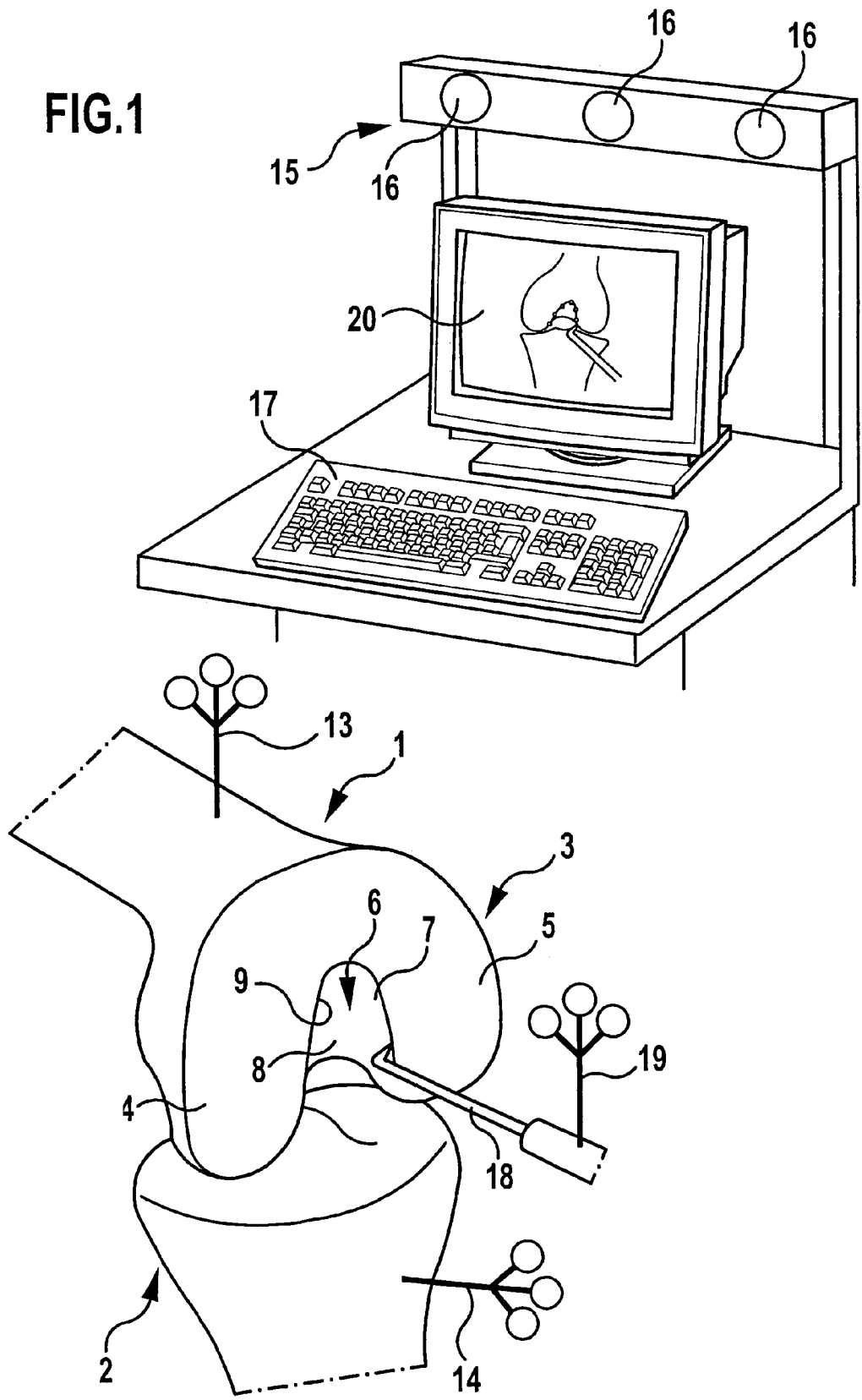
FIG. 1 shows a schematic view of a bent knee joint, with a navigation system for determining the position of the femur, the tibia and a sensing element.

Represented in the drawing are the distal end of a femur 1 and the proximal end of a tibia 2, which together form a knee joint 3; the other parts of the knee joint have been omitted for clarity. In this region, the femur 1 forms two adjacent areas of the joint, the condyles 4, 5, which between them form a cavity. This cavity is usually referred to as the notch 6. This notch is bounded laterally by side surfaces 7 of the condyles 4, 5. On the upper side there extends a roof 8 running obliquely in relation to the longitudinal axis of the femur 1. On the front side, that is the anterior side, the notch 6 is closed, whereas to the rear side of the knee joint, that is the posterior side, it is open. Toward the areas of the joint that are the condyles 4, 5, the notch 6 is bounded by an approximately U-shaped front edge 9. This forms the transition between an osseous region and a cartilaginous region and is easy for the surgeon to feel and therefore locate.

Figure 4:
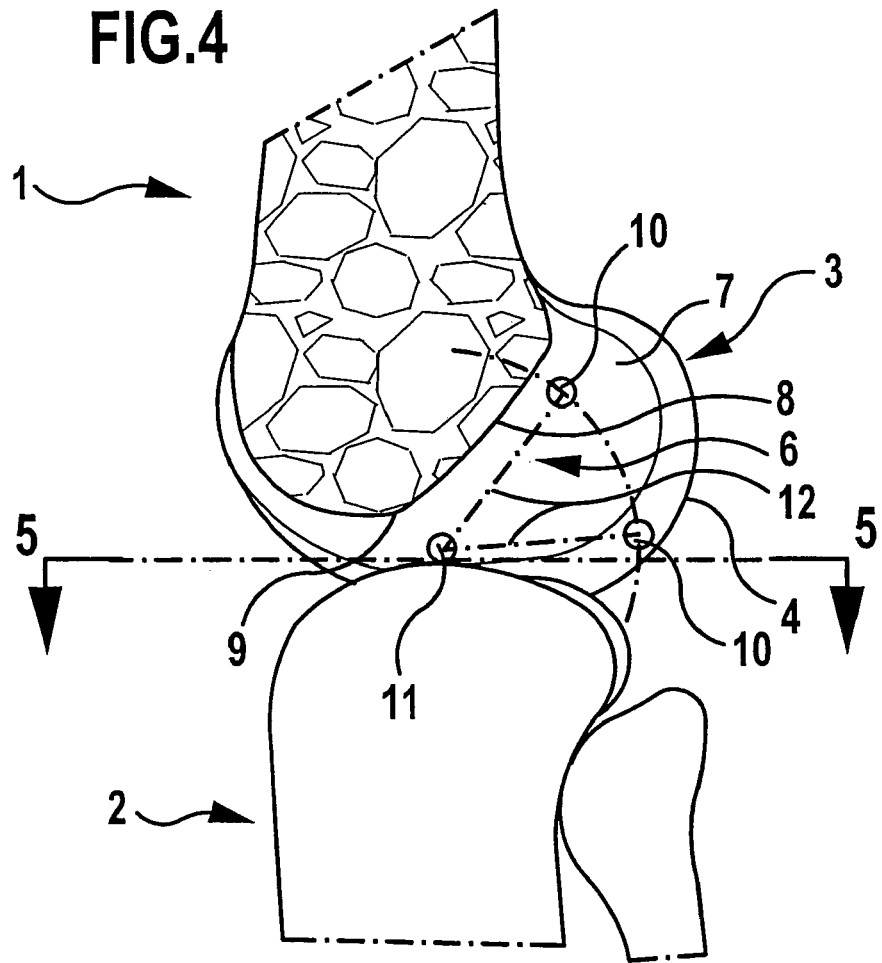
FIG. 4 shows a view similar to FIG. 2 with the knee joint straight.

The femur 1 and the tibia 2 are joined to each other by a number of ligaments. The present case is only concerned with the so-called anterior cruciate ligament, which extends in the intercondylar cavity, that is in the notch 6, and on the femur side is connected to the femur 1 at a point 10 disposed at the posterior end of the notch 6, on the tibia side is connected at a point referred to hereafter as the exit point 11, which is offset in the anterior direction with respect to the point 10. In FIG. 4, the point 10 and the exit point 11 are schematically represented; the line 12 joining the point 10 and the exit point 11 shows the course of the anterior cruciate ligament with the knee straight (point 10 is in the high position) and with the knee bent (point 10 is in the lowered position).

In order to replace the anterior cruciate ligament by an implant, which may for example be an artificial implant or a piece of ligament that has been taken from elsewhere in the body, it is necessary to determine the position both of the point 10 and of the exit point 11. The position of the point 10 is determined substantially by maintaining the isometry during movement, that is with minimal change in length of the implant. In the case of the position of the exit point 11, care must be taken that the implant does not come into contact with the osseous structure of the femur 1, in particular with the front edge 9, after implantation.

In order to achieve this, fixed on the femur 1 and the tibia 2 are marking elements 13, 14, which have for example three balls reflecting infrared radiation and are respectively rigidly connected to the femur and the tibia. Marking elements 13 and 14 of this type are part of a navigation system 15 known per se, which captures radiation reflected from the marking elements by means of a camera system with three cameras 16 and on this basis determines the position and location of the marking elements 13 and 14 in space and consequently naturally also the position and location of the femur 1 and the tibia 2. The corresponding positional data are fed in the navigation system 15 to a data-processing system 17 and can be stored there and used for subsequent calculations.

To establish the position of the front edge 9 in the knee joint 3, also used is a sensing element 18, for example a simple sensing hook, to which there is fastened a further marking element 19 of the same type, the position of which can likewise be determined by the navigation system 15. It is possible as a result to establish the location and position of the sensing element 18 precisely at any time.

Figure 2:
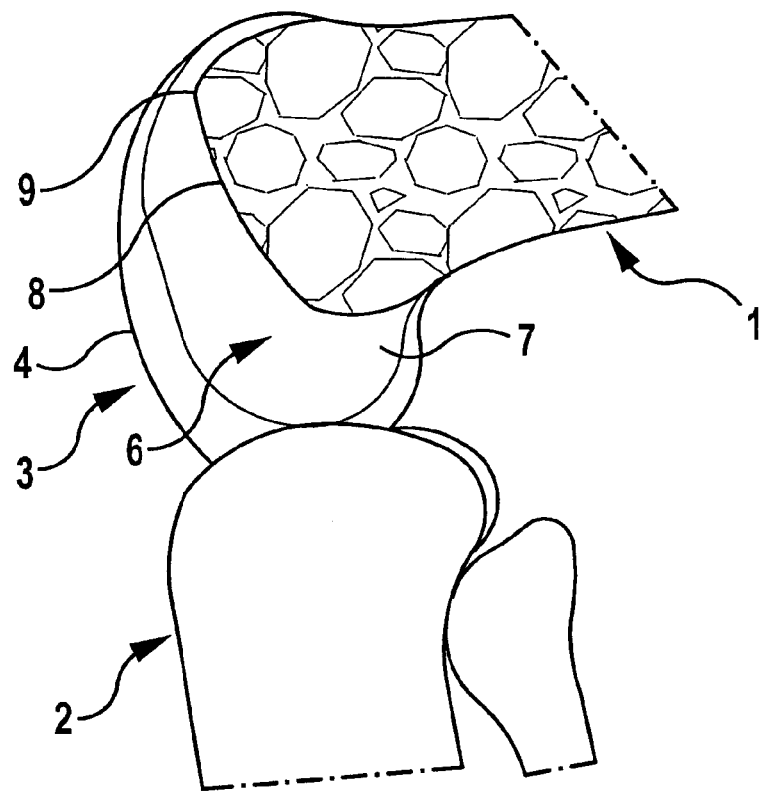
FIG. 2 shows a schematic sectional view through a knee joint in the bent position.
Figure 3:
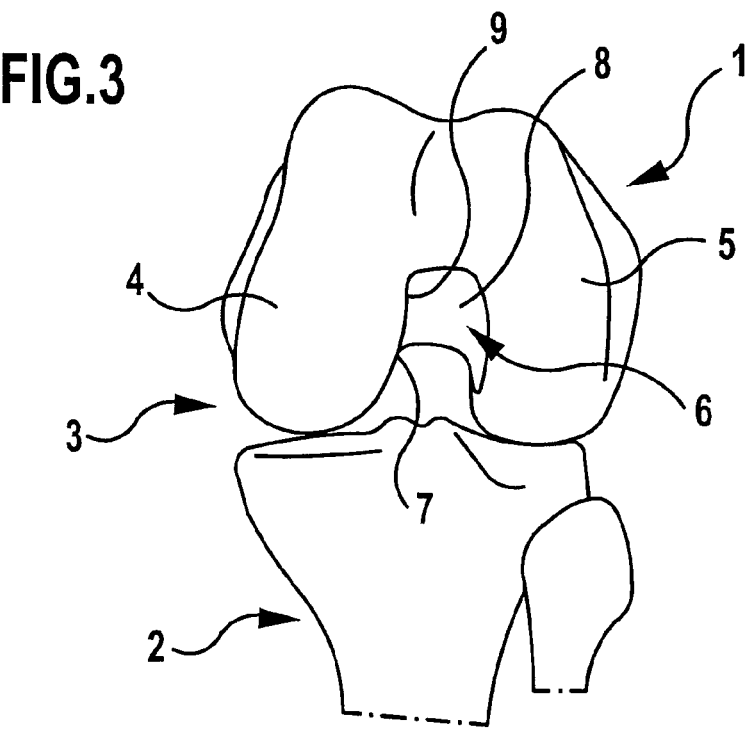
FIG. 3 shows a schematic front view of the bent knee joint of FIG. 2.

To establish the tibial exit point 11, firstly the knee joint 3 is bent in such a way that the front edge 9 of the notch 6 is freely accessible, which is represented in FIGS. 1 to 3. The sensing element 18 is moved to quite a large number of individual points on the front edge and their positional data are stored in the data-processing system 17. To make this easier for the surgeon, the course of such a front edge can be schematically presented on a screen 20 of the data-processing system 17. Marked on this front edge are individual points that show the surgeon at which locations the sensing element 18 is to be placed on the front edge 9. When positional data have been determined at such a location and stored, this can be indicated to the surgeon on the screen 20, for example by the corresponding points changing in color, so that the surgeon is guided through scanning the front edge 9 in such a way that he targets measuring points, and determines the positional data, at equal intervals over the entire length of this front edge. These positional data are stored together in the memory and describe the course of the front edge on the femur 1.

In a further step, the leg is swung into the straight position, as represented in FIG. 4. As this happens, the movements of the femur 1 and the tibia 2 in relation to each other are tracked by the marking elements 13 and 14; corresponding positional data records can be stored.

The longitudinal axis of the tibia 2 is entered into the data-processing system 17 in a suitable way, which may take place for example in a way known per se by determining the position of the corresponding joints by movement of the leg about the knee joint 3 and about the ankle, a line joining these joints then corresponding to the longitudinal axis of the tibia 2. In the same way, the longitudinal axis of the femur 1 can be determined in a way known per se by movements of the leg about the hip joint and the knee.

The course of a plane which is perpendicular to the longitudinal axis of the tibia and extends in the region of the proximal end of the tibia 2, for example a few millimeters below the highest point of the proximal end of the tibia, is then calculated in the data-processing system. Such a plane, like the one which is indicated for example by the section line 5-5 in FIG. 4, is referred to hereafter as the projection plane 21.

In a next step, with the leg straight, the data-processing system projects the positional data for the front edge 9 onto the projection plane 21 and thereby produces an approximately U-shaped projection line 22, the course of which depends on the disposition and extent of the front edge 9. The projection line 22 encloses with its U-shaped course a region 23 on the projection plane 21, which is referred to hereafter as the permitted region.

The implant which is intended to replace the anterior cruciate ligament is preferably circular in cross-section; for example, the diameter of the implant may be 6 mm to 10 mm, preferably approximately 8 mm.

The selected diameter of the implant is entered in the data-processing system via a keyboard, and the data-processing system then produces in the projection plane 21 a circular area 24 which marks the position of the exit point 11.

Figure 5:
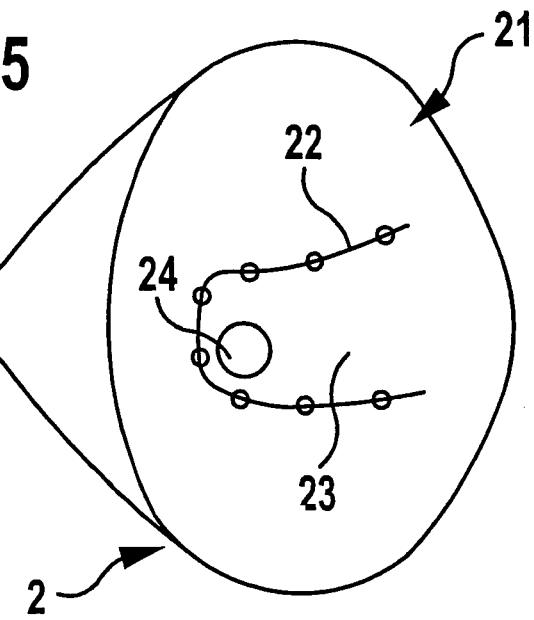
FIG. 5 shows a sectional view along line 5-5 in FIG. 4.

The projection plane 21 with the projection line 22 and the circular area 24 is presented on the screen 20 by the data-processing system 17, so that the surgeon can see precisely whether the circular area 24 lies in the permitted region or lies partly outside it. The representation on the screen 20 corresponds to the representation of FIG. 5. By suitable means, for example a joystick or a mouse, the circular area 24 can be displaced in the projection plane 21. Since the closed end of the projection line 22 points toward the front side of the knee, and since the exit point 11 is to be disposed as far as possible in the anterior direction to increase stability, the surgeon will displace the circular area 24 as much as possible to the anterior end of the projection line 22, but at the same time pay close attention to ensuring that the entire circular area 24, which corresponds to the cross-section of the implant, remains within the permitted region and does not intersect the projection line. When an optimum position of the circular area 24 has been determined in this way, the center point of this circular area 24 can be determined. This center point corresponds to the exit point 11. In this way, the surgeon has determined a point at which he can connect the implant to the tibia 2, for example by drilling a hole which coincides with the circular area 24 and into which the implant is drawn and fixed within said hole. It is then ensured that the implant exits from the tibia 2 in a region of the tibial surface that permits free movement of the implant without it touching the osseous structure of the femur when the femur and the tibia are moved with respect to each other.

The positioning of the circular area 24 in the permitted region can be carried out automatically by the data-processing system, but it is advantageous if the surgeon has options here, since he may possibly also be able to use other optimization criteria, on the one hand to determine an optimal exit point 11 and on the other hand to ensure that contacts of the implant with the femur between the exit point 11 and the point 10 are avoided.

The invention claimed is:

1. Method for determining a position on an upper side of a tibia of an exit point of an implant replacing an anterior cruciate ligament of a knee joint of a leg, in which positional data of the tibia and a femur are determined by means of a navigation system, in which geometrical form data of the femur in a region of the femur facing an upper side of the tibia are recorded and in which the form data are processed together with the positional data of the tibia and the femur in a data-processing system to calculate positional data for the exit point, comprising:

with the leg bent, detecting respective positions of a number of points along a front edge of a notch formed by condyles of the femur such that position and progression of the points on the femur are determined, with the leg straight, projecting a course of the front edge of the notch in the form of a curve onto a projection plane which is perpendicular to a longitudinal axis of the tibia in a region of the upper side of the tibia, within a region enclosed by this projected curve, selecting the exit point such that the exit point maintains at least a distance corresponding to a radius of the implant from the projected curve, and selecting a position of the exit point in which the exit point lies as far as possible in a front part of the region enclosed by the projected curve and as close as possible to the projected curve.

2. Method for determining a position on an upper side of a tibia of an exit point of an implant replacing an anterior cruciate ligament of a knee joint of a leg, in which positional data of the tibia and a femur are determined by means of a navigation system, in which geometrical form data of the femur in a region of the femur facing an upper side of the tibia are recorded and in which the form data are processed together with the positional data of the tibia and the femur in a data-processing system to calculate positional data for the exit point, comprising:

with the leg bent, detecting respective positions of a number of points along a front edge of a notch formed by condyles of the femur such that position and progression of the points on the femur are determined, with the leg straight, projecting a course of the front edge of the notch in the form of a curve onto a projection plane which is perpendicular to a longitudinal axis of the tibia in a region of the upper side of the tibia, and within a region enclosed by this projected curve, selecting the exit point such that the exit point maintains at least a distance corresponding to a radius of the implant from the projected curve;

wherein:

a circular area of a diameter corresponding to a diameter of the implant used is projected into the projection plane, this circular area is displaced in an area enclosed by the projected curve such that the circular area does not intersect the projected curve, and in one of multiple positions of the circular area achieved by such displacement, a center point of the circular area is selected as the exit point for the implant.

3. Method according to claim 2, wherein a navigated sensor is used for recording the positional data for the points located on the front edge of the notch.

4. Method according to claim 2, wherein, during the detecting of the position of the points on the front edge of the notch, an image of the front edge is shown on an image display of the data-processing system and the points for which the positional data are to be recorded are marked on the image display.

5. Method according to claim 2, wherein:

the projected curve and the region enclosed by the projected curve are presented on an image display, a desired position for the exit point is selected on the image display by means of a displaceable image of a display element, and corresponding positional data are stored in the data-processing system.

6. Method according to claim 5, wherein a circle of a diameter corresponding to a diameter of the implant used is selected as the display element.

7. Apparatus for determining a position on an upper side of a tibia of an exit point of an implant replacing an anterior cruciate ligament of a knee joint of a leg, comprising:

a navigation system, marking elements adapted to be fixedly connected to a femur and the tibia, a navigated sensor, and a data-processing system which comprises:

a memory, and a computer unit, wherein:

positional data for a number of points along a front edge of a notch formed by condyles of the femur are detected by the navigation system and are stored in the memory, the computer unit is programmed such that it projects the positional data stored in the memory, and with the positional data a course of the front edge of the notch with the leg straight, onto a projection plane in a region of an upper side of the tibia, the plane being perpendicular to a longitudinal axis of the tibia, producing a U-shaped projected curve which encloses a region in which the exit point is located, the computer unit is programmed such that it projects a circular area of a diameter corresponding to a diameter of the implant used into the projection plane and displaces the circular area in an area enclosed by the projected curve such that the circular area does not intersect the projected curve, and in one of multiple positions of the circular area achieved by such displacement, the computer unit selects a center point of the circular area as the exit point for the implant.

8. Apparatus according to claim 7, wherein the computer unit is programmed such that it selects a position for the exit point in which the exit point lies as far as possible in a front part of the region enclosed by the projected curve and as close as possible to the projected curve.

9. Apparatus according to claim 7, wherein the computer unit of the data-processing system is programmed such that, during the detection of the position of points on the front edge of the notch, the computer unit forms an image of the front edge on an image display of the data-processing system and marks on the image display the points for which the positional data are to be recorded.

10. Apparatus according to claim 7, wherein the computer unit is programmed such that it:

presents the projected curve and the region enclosed by the projected curve on an image display, presents a displaceable image of a display element for a selected position of the exit point on the image display, and stores the corresponding positional data for the selected position in the memory.

11. Apparatus according to claim 10, wherein the display element is a circular area of a diameter corresponding to a diameter of the implant used.

\* \* \* \* \*

UNITED STATES PATENT AND TRADEMARK OFFICE
CERTIFICATE OF CORRECTION

| | |
|---|---|
| PATENT NO. | : 7,643,868 B2 |
| APPLICATION NO. | : 11/086995 |
| DATED | : January 5, 2010 |
| INVENTOR(S) | : Giordano et al. |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1325 days.

Signed and Sealed this

Sixteenth Day of November, 2010

David J. Kappos
*Director of the United States Patent and Trademark Office*

UNITED STATES PATENT AND TRADEMARK OFFICE
CERTIFICATE OF CORRECTION

| | | |
|---|---|---|
| PATENT NO. | : 7,643,868 B2 | |
| APPLICATION NO. | : 11/086995 | |
| DATED | : January 5, 2010 | |
| INVENTOR(S) | : Giordano et al. | |

It is certified that error appears in the above-identified patent and that said Letters Patent is hereby corrected as shown below:

On the Title Page, under (75) Inventors, the city of residence for inventor Juergen Eichhorn is corrected to read: -- Mitterfels/Scheibelsgrub --.

Signed and Sealed this
Eighteenth Day of January, 2011

David J. Kappos
*Director of the United States Patent and Trademark Office*